United States Patent
Nitta et al.

(10) Patent No.: US 9,623,203 B2
(45) Date of Patent: Apr. 18, 2017

(54) RESPIRATORY ASSISTANCE DEVICE WITH BLOWER PLACED ABOVE THE MOUTH OF A USER

(71) Applicant: Metran Co., Ltd., Kawaguchi-shi, Saitama (JP)

(72) Inventors: Kazufuku Nitta, Saitama (JP); Shinichi Shiota, Saitama (JP); Masashi Higashiura, Tokyo (JP)

(73) Assignee: METRAN CO., LTD., Kawaguchi-shi, Saitama (JP)

( * ) Notice: Subject to any disclaimer, the term of this patent is extended or adjusted under 35 U.S.C. 154(b) by 299 days.

(21) Appl. No.: 14/238,809

(22) PCT Filed: Dec. 2, 2013

(86) PCT No.: PCT/JP2013/082331
§ 371 (c)(1),
(2) Date: Feb. 13, 2014

(87) PCT Pub. No.: WO2014/129043
PCT Pub. Date: Aug. 28, 2014

(65) Prior Publication Data
US 2015/0217073 A1    Aug. 6, 2015

(30) Foreign Application Priority Data
Feb. 21, 2013 (JP) ................................. 2013-031714

(51) Int. Cl.
*A61M 16/06* (2006.01)
*A61M 16/00* (2006.01)
*A61M 16/20* (2006.01)

(52) U.S. Cl.
CPC .... *A61M 16/0666* (2013.01); *A61M 16/0066* (2013.01); *A61M 16/06* (2013.01);
(Continued)

(58) Field of Classification Search
CPC .............. A61M 16/0066; A61M 16/06; A61M 16/0666; A61M 16/20; A61M 16/202
See application file for complete search history.

(56) References Cited

U.S. PATENT DOCUMENTS

| 6,017,016 A | * | 1/2000 | Jackson | F15C 3/14 251/129.06 |
| 6,032,665 A | * | 3/2000 | Psaros | A61M 16/12 128/203.12 |

(Continued)

FOREIGN PATENT DOCUMENTS

| EP | 2 090 781 A1 | | 8/2009 |
| JP | 26-6584 | * | 10/1951 |

(Continued)

OTHER PUBLICATIONS

European Patent Office Search Report issued in Application No. EP 13 87 5619 dated Nov. 30, 2015 (4 pages).

(Continued)

*Primary Examiner* — Kathryn E Ditmer
(74) *Attorney, Agent, or Firm* — Flynn, Thiel, Boutell & Tanis, P.C.

(57) ABSTRACT

A respiratory assistance device including a pair of prongs which are airways to be attached to a user's nose, and a blower which is connected to the pair of prongs and sends air to the user's nasal cavity via the prongs. The blower is placed on and is in contact with the user's mouth. The blower includes a housing including an intake port from which gas is taken in, a flow channel through which the air taken in via the intake port flows, and a discharge port which sends the air flowing through the flow channel toward the prongs, an impeller arranged in the housing so that its front side faces the intake port, and a partition member arranged on a rear side of the impeller so that a slit is formed along (Continued)

an inner periphery of the housing thereby partitioning the rear side into a space where the impeller is arranged.

6 Claims, 11 Drawing Sheets

(52) U.S. Cl.
CPC ......... *A61M 16/205* (2014.02); *A61M 16/208* (2013.01); *A61M 2016/0027* (2013.01); *A61M 2016/0039* (2013.01); *A61M 2205/0294* (2013.01); *A61M 2205/15* (2013.01); *A61M 2205/42* (2013.01); *A61M 2205/52* (2013.01); *A61M 2206/11* (2013.01); *A61M 2209/088* (2013.01)

(56) References Cited

U.S. PATENT DOCUMENTS

| | | | | |
|---|---|---|---|---|
| 2003/0000531 | A1* | 1/2003 | Tuck | A61M 16/0069 128/205.25 |
| 2006/0112962 | A1* | 6/2006 | Tebbutt | A61M 16/0488 128/206.29 |
| 2006/0255064 | A1* | 11/2006 | Donaldson | A61M 5/142 222/95 |
| 2008/0178879 | A1* | 7/2008 | Roberts | A61M 16/0066 128/204.18 |
| 2008/0216831 | A1* | 9/2008 | McGinnis | A61M 16/00 128/204.21 |
| 2010/0170513 | A1 | 7/2010 | Bowditch et al. | |
| 2011/0284005 | A1 | 11/2011 | Cewers | |
| 2012/0157794 | A1* | 6/2012 | Goodwin | A61B 5/0826 600/301 |
| 2012/0234323 | A1* | 9/2012 | Connor | A61M 16/0066 128/204.21 |
| 2014/0069432 | A1* | 3/2014 | Mebasser | A61M 16/0066 128/205.25 |

FOREIGN PATENT DOCUMENTS

| | | |
|---|---|---|
| JP | 26-6584 B | 10/1951 |
| JP | 4497809 B2 | 7/2003 |
| JP | 2006-214493 A | 8/2006 |
| JP | 2007-506482 A | 3/2007 |
| JP | 2011-156410 A | 8/2011 |
| JP | 2013-501541 A | 1/2013 |
| WO | WO 2008/069266 A1 | 6/2008 |
| WO | WO 2011/017763 A1 | 2/2011 |
| WO | WO 2011/050059 A1 | 4/2011 |

OTHER PUBLICATIONS

Metran Co., Ltd. [online], Products > Jusmine, [searched on Jun. 29, 2012], the Internet (URL: http://www.metran.co.jp/products/products2/190.html)). with partial translation (4 pages).

* cited by examiner

-PRIOR ART-

Fig. 14
(A)
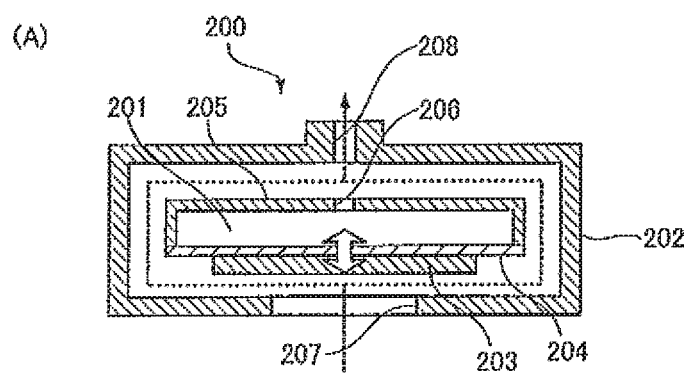
-PRIOR ART-
(B)
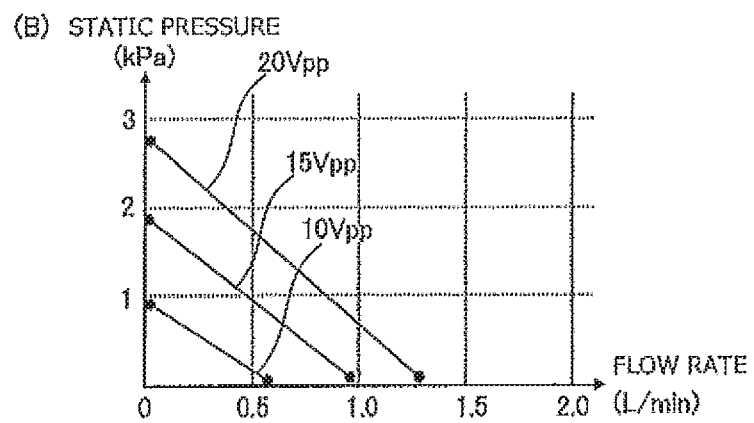

RESPIRATORY ASSISTANCE DEVICE WITH BLOWER PLACED ABOVE THE MOUTH OF A USER

TECHNICAL FIELD

The present invention relates to a respiratory assistance device.

BACKGROUND ART

Sleep apnea occurs when the airway muscle relaxes and the root of the tongue or the soft palate lowers to obstruct the airway during sleep. For patients with this type of respiration disorder, respiratory assistance devices including a blower for applying positive pressure to the airway are used (see Japanese Translation of PCT Patent Application Publication No. 2007-506482, Japanese Patent Application Laid-Open No. 2011-156410, and non-patent document (Metran Co., Ltd., [online], Products>Jusmine, [searched on Jun. 29, 2012], the Internet).

SUMMARY OF INVENTION

Technical Problem

In the respiratory assistance devices according to Japanese Translation of PCT Patent Application Publication No. 2007-506482, Japanese Patent Application Laid-Open No. 2011-156410, the blower is integrated with a mask that covers the mouth and nose of the user. This shortens the path from the blower to the airway for improved responsiveness. Meanwhile, the user's face undergoes the weight of the blower, which is burdensome.

The present invention has been achieved in view of the foregoing problem, and it is an object thereof to provide a respiratory assistance device which reduces the burden on the user.

Solution to Problem

The present invention provides a respiratory assistance device including: a prong that is an airway to be attached to a user's nose; and a blower that is connected to the prong and sends gas to the user's nasal cavity via the prong, wherein the blower is placed on the user's mouth.

Alternatively, the present invention provides a respiratory assistance device including: a prong that is an airway to be attached to a user's nose; and a blower that is connected to the prong and sends gas to the user's nasal cavity via the prong, wherein the blower is placed on the user's mouth so as to be in contact with the mouth, and helps keep the mouth closed.

The present invention also provides a respiratory assistance device including: a mask that covers a user's mouth and nose; and a blower that is arranged inside the mask and sends gas to the user's nasal cavity, wherein the blower is placed on the user's mouth.

Alternatively, the present invention provides a respiratory assistance device including: a mask that covers a user's mouth and nose; and a blower that is arranged inside the mask and sends gas to the user's nasal cavity, wherein the blower is placed on the user's mouth so as to be in contact with the mouth, and helps keep the mouth closed.

According to the foregoing inventions, the distance from the center axis of the user's body to the center of gravity of the blower can be reduced as compared to heretofore. This can reduce the moment of the blower when the user in bed turns over or turns his/her face. Since the blower is placed on the mouth, the user can turn over or turn his/her face without pressing the blower against the pillow with his/her face. As a result, the burden on the user can be reduced.

Suppose that the blower is placed on cheeks. In such a case, the blower can be pressed against the pillow and the like by the cheeks (face) when the user turns over or turns his/her face. This is burdensome to the user. In other words, the blower essentially needs to be placed on the centerline of the body. Among positions on the centerline, the blower is placed on the mouth which is less disturbing to the user.

The present invention also provides the respiratory assistance device according to the foregoing means, wherein the blower is in contact with the user's mouth.

The present invention also provides the respiratory assistance device according to the foregoing means, wherein the blower keeps the user's mouth closed.

According to the foregoing inventions, the blower can hold the user's mouth to help to keep the mouth closed. This produces a mouth-closed state which is desirable during nasal breathing, whereby the burden on the user is reduced. Note that the contact with the mouth may be either direct or indirect.

The present invention also provides the respiratory assistance device according to the foregoing means, wherein the blower includes: a housing including an intake port from which the gas is taken in, a flow channel that is arranged to extend around and through which the gas taken in via the intake port flows, and a discharge port that sends the gas flowing through the flow channel toward the prong; an impeller that is arranged in the housing so that its front side faces the intake port; and a partition member that is arranged on a rear side of the impeller so that a slit extending around is formed along an inner periphery of the housing, thereby partitioning the rear side into a space where the impeller is arranged and the flow channel which extends around along the slit.

According to the foregoing invention, a two-stage structure including the space where the impeller is arranged and the flow channel leading to the discharge port is employed. An airflow taken in via the intake port can thus be separated from an airflow to be sent out via the discharge port. This can avoid collision between the airflow taken in via the intake port and the airflow to be sent out via the discharge port. In other words, the occurrence of noise due to the collision of the airflows can be prevented.

The flow of the air through the slit connecting the space where the impeller is arranged and the flow channel produces noise. Such noise can cancel other noise occurring from the rotation of the impeller. As a result, a burden on the user due to noise can be reduced.

The present invention also provides the respiratory assistance device according to the foregoing means, including an exhalation valve that is arranged to cover an air hole formed in a path from the blower to the user's nose, wherein: the exhalation valve includes a piezoelectric element that makes a displacement according to an amount of voltage applied; and the piezoelectric element makes a displacement to draw apart from or approach to make contact with a surface constituting the flow channel, whereby the piezoelectric element itself opens and closes the air hole.

According to the foregoing invention, the exhalation valve includes the piezoelectric element, and the amount of opening thereof can be finely adjusted. This can avoid a sharp change in the flow rate of exhaled air released via the exhalation valve. In other words, a sharp change in the air pressure in the path from the blower to the user's nose can be prevented. This can prevent an increase in the burden on the user.

The exhalation valve can be closed so that the interior of the path becomes air tight during breathing in. The amount of gas leaking via the exhalation valve can thus be reduced. Since the exhalation valve includes the piezoelectric element, responsiveness is high and the burden on the user is small. Specifically, if a solenoid valve is used as the exhalation valve, the exhalation valve opens and closes in about 8 msec to 10 msec of time. If the exhalation valve includes the piezoelectric element like the foregoing invention, the exhalation valve can open and close in a time as short as about 100 μsec.

Moreover, since the exhalation valve includes the piezoelectric element, the exhalation valve has a longer endurance time and is more difficult to break than when a solenoid valve is used as the exhalation valve. Furthermore, since the exhalation valve includes the piezoelectric element, the respiratory assistance device can be miniaturized in size and reduced in weight as compared to cases such as when a solenoid valve is used as the exhalation valve. The gravitational force of the respiratory assistance device acting on the face of the user can thus be reduced to reduce the burden on the user.

The present invention also provides the respiratory assistance device according to the foregoing means, wherein the exhalation valve makes a displacement within the path.

According to the foregoing invention, the exhalation valve can be prevented from interfering with other objects when opening and closing. As a result, the exhalation valve can be prevented from malfunctioning.

Advantageous Effects of the Invention

According to the respiratory assistance device of the present invention, an excellent effect of reducing the burden on the user can be obtained.

BRIEF DESCRIPTION OF DRAWINGS

FIG. 9(A) shows a state when an exhalation valve is open, and FIG. 9(B) shows a state when the exhalation valve is closed.

FIG. 11(A) shows a case with the respiratory assistance device according to the first embodiment, and FIG. 11(B) shows a case with a conventional respiratory assistance device.

FIG. 12(A) shows a case with a respiratory assistance device according to a second embodiment, and FIG. 12(B) shows a case with the conventional respiratory assistance device.

FIG. 14(A) is a sectional view showing a configuration example of a micro pump, and FIG. 14(B) is a graph showing pressure-flow rate lines of the micro pump.

DESCRIPTION OF INVENTION

Hereinafter, a respiratory assistance device according to the present invention will be described in detail with reference to the drawings.

First Embodiment

Figure 1:
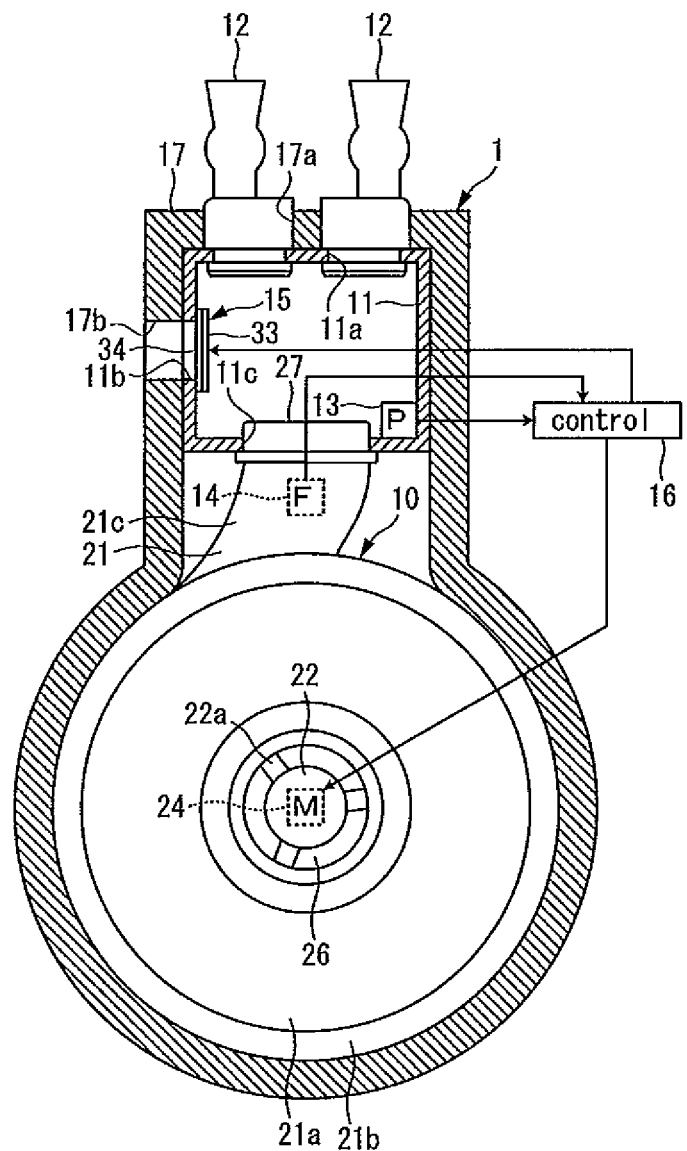
FIG. 1 is a sectional view of a respiratory assistance device according to a first embodiment of the present invention.
Figure 2:
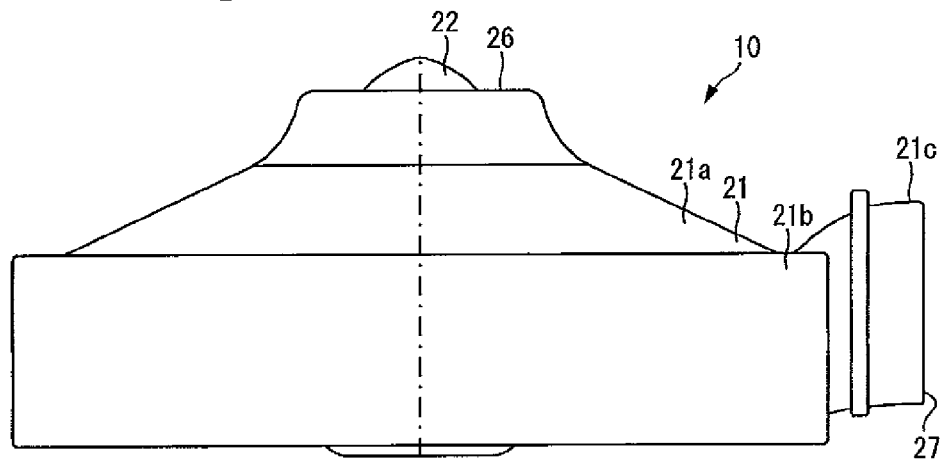
FIG. 2 is a side view of a blower.
Figure 3:
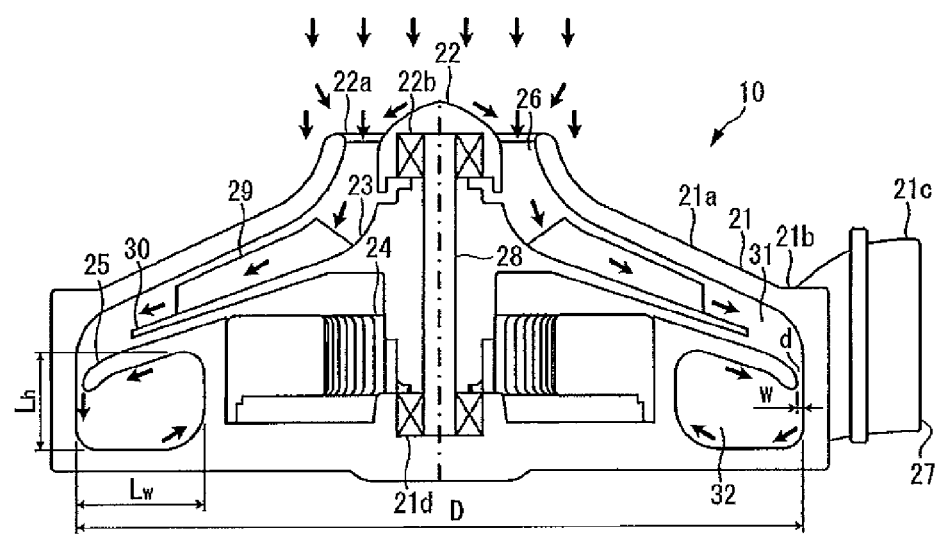
FIG. 3 is a sectional view of the blower.
Figure 4:
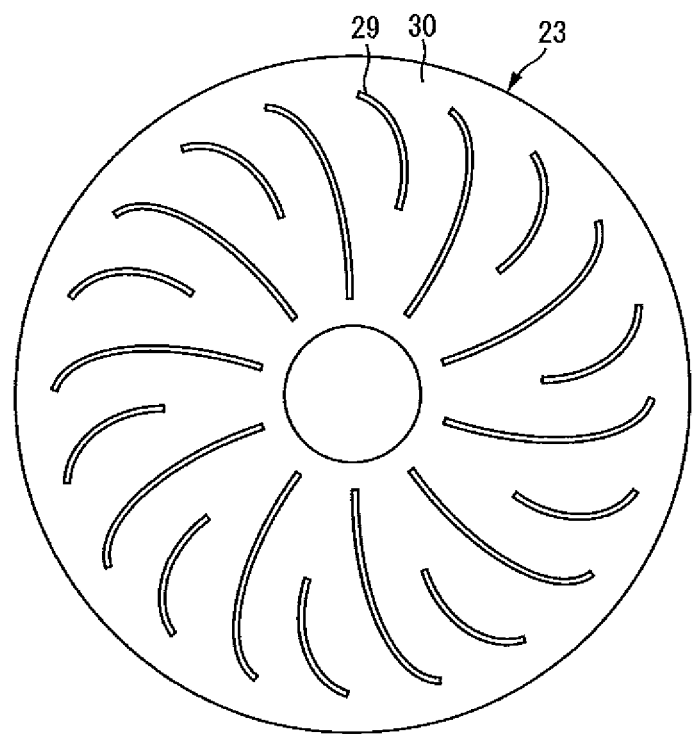
FIG. 4 is a front view of an impeller.
Figure 5:
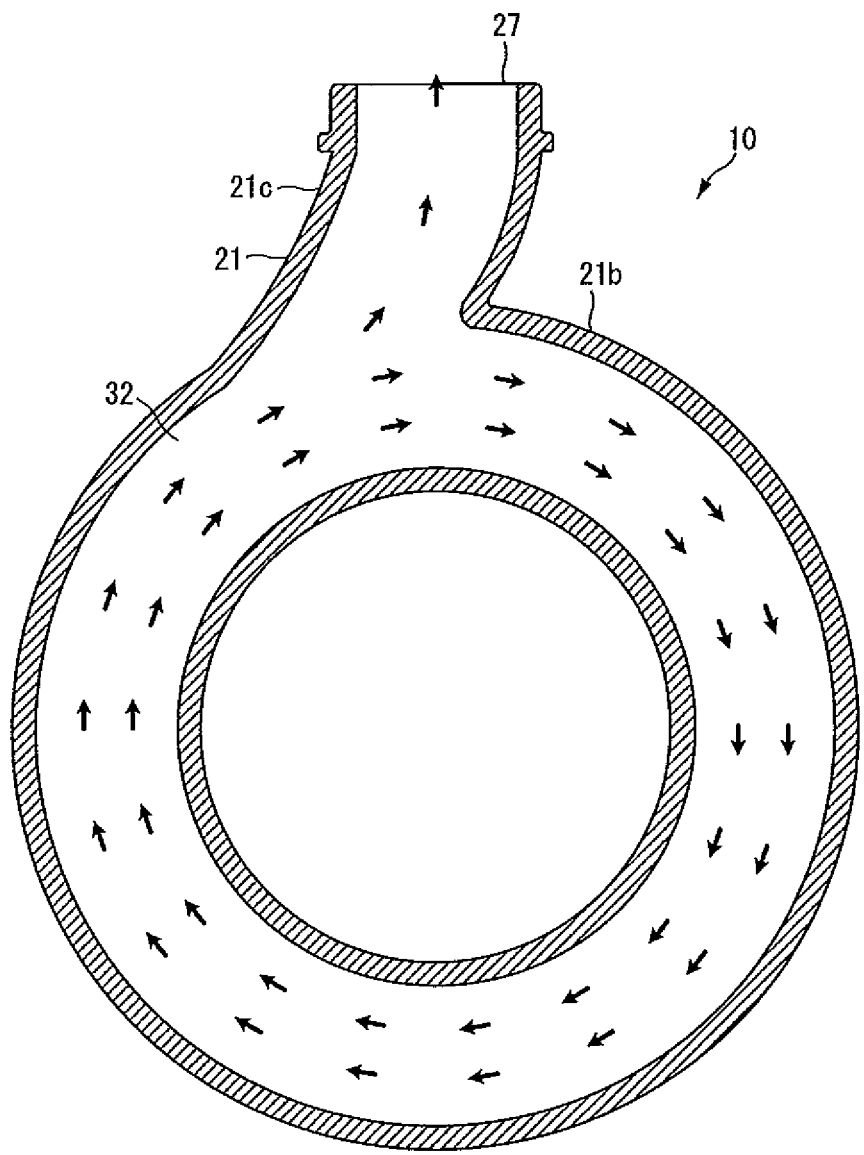
FIG. 5 is a sectional view of a flow channel.
Figure 6:
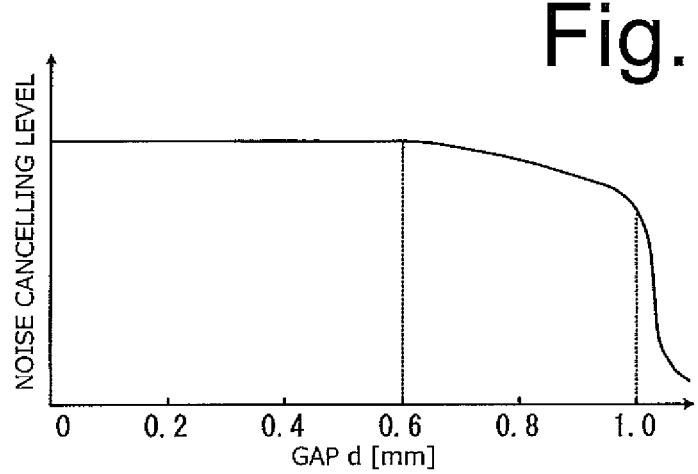
FIG. 6 is a graph showing a relationship between a width of a slit extending around along an inner periphery of a housing and a noise cancelling level, in which the horizontal axis indicates the width of the slit and the vertical axis indicates the noise cancelling level.
Figure 7:
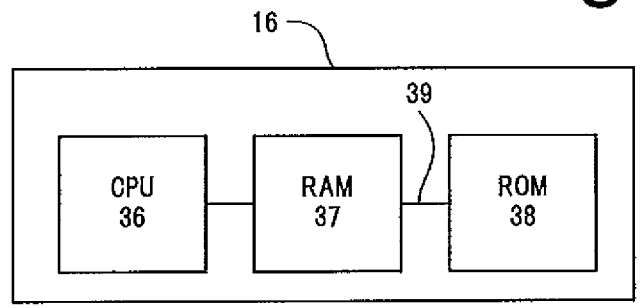
FIG. 7 is a block diagram showing a hardware configuration of a control unit.
Figure 8:
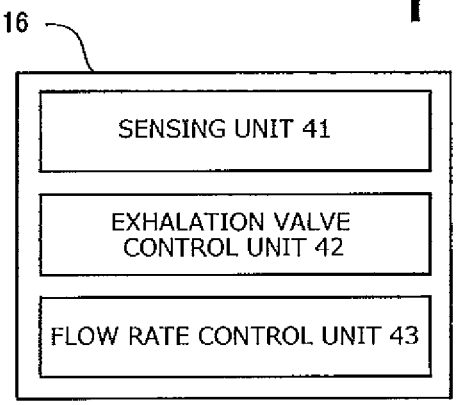
FIG. 8 is a schematic diagram showing a functional configuration of the control unit.
Figure 9:
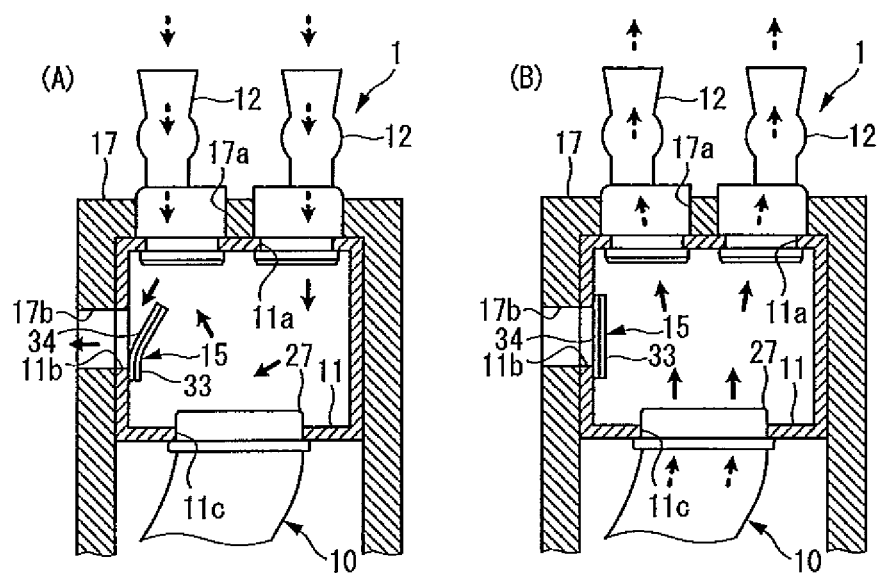
FIGS. 9(A) and 9(B) are sectional views of a chamber portion.
Figure 10:
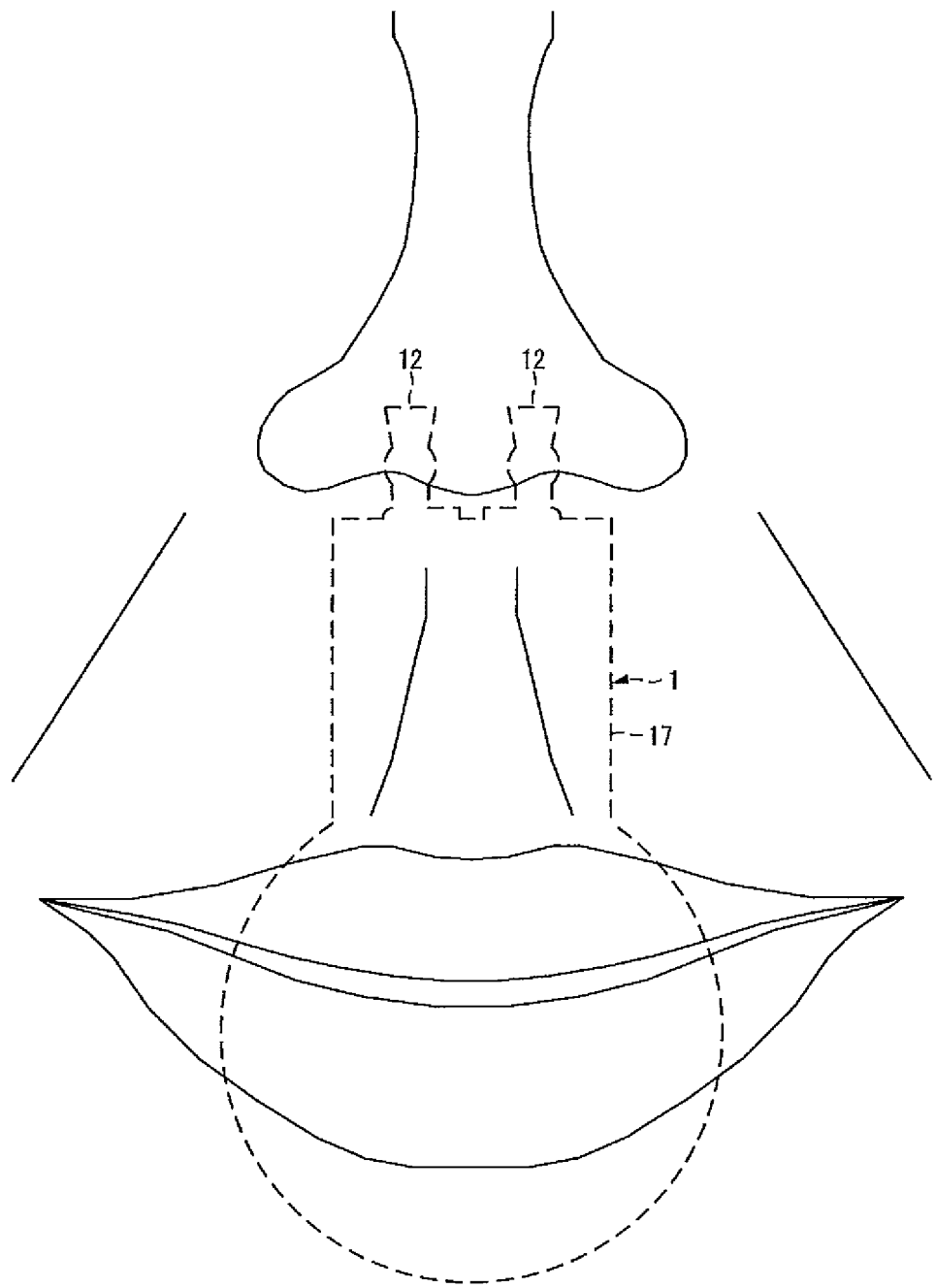
FIG. 10 is a diagram showing a use state of the respiratory assistance device.
Figure 11:
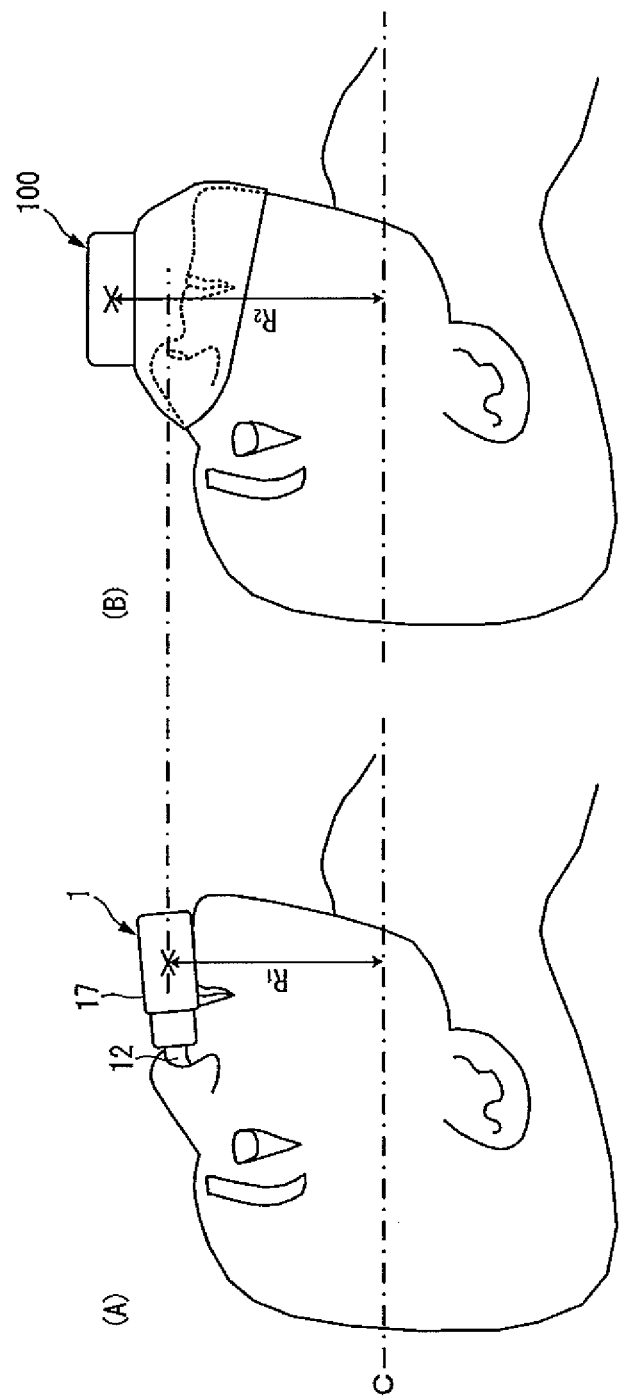
FIGS. 11(A) and 11(B) are diagrams showing use states of respiratory assistance devices for explaining moment.

A configuration of a respiratory assistance device 1 according to a first embodiment of the present invention will initially be described with reference to FIGS. 1 to 11(B). FIG. 1 is a sectional view of the respiratory assistance device 1. FIG. 2 is a side view of a blower 10. FIG. 3 is a sectional view of the blower 10. FIG. 4 is a front view of an impeller 23. FIG. 5 is a sectional view of a flow channel 32. FIG. 6 is a graph showing a relationship between a width w of a slit d extending around along an inner periphery of a housing 21 and a noise cancelling level, in which the horizontal axis indicates the width w of the slit d and the vertical axis indicates the noise cancelling level. FIG. 7 is a block diagram showing a hardware configuration of a control unit 16. FIG. 8 is a schematic diagram showing a functional configuration of the control unit 16. FIGS. 9(A) and 9(B) are sectional views of a chamber 11 portion, FIG. 9(A) shows a state when an exhalation valve 15 is open, and FIG. 9(B) shows a state when the exhalation valve 15 is closed. FIG. 10 is a diagram showing a use state of the respiratory assistance device 1. FIGS. 11(A) and 11(B) are diagrams showing use states of respiratory assistance devices for explaining moment, FIG. 11(A) shows a case with the respiratory assistance device 1, and FIG. 11(B) shows a case with a conventional respiratory assistance device 100. In the drawings, some of the components, hatchings representing cross sections, and the like are omitted as appropriate to simplify the drawings. In the drawings, members are expressed in exaggerated sizes if needed.

The respiratory assistance device 1 shown in FIG. 1 is intended to produce a positive pressure in an airway, and is used by a patient with respiration disorder. This respiratory assistance device 1 is of so-called prong type. Specifically, the respiratory assistance device 1 includes a blower 10, a chamber 11, a pair of prongs 12, an air pressure meter 13, a flowmeter 14, an exhalation valve 15, a control unit 16, and a case 17.

The blower 10 shown in FIGS. 2 to 5 is connected to the pair of prongs 12 via the chamber 11. This blower 10 sends air to the user's nasal cavity (airway) via the pair of prongs 12. The blower 10 thereby produces a positive pressure in the airway. Specifically, the blower 10 includes a housing 21, a rectifying member 22, an impeller 23, a motor 24, and a partition member 25.

The housing 21 is a resin-molded main body of the blower 10, and includes an upper part 21a having a generally circular truncated conical shape in appearance, a lower part 21*b* having a generally circular cylindrical outer shape, and a discharge pipe 21*c* extending sideways from the lower part 21*b*. The upper part 21*a* is smoothly curved upward. The upper part 21*a* has a circular intake port 26 in the top. A bearing 21*d*, which functions as a bearing for supporting a rotating shaft 28 of the impeller 23, is embedded in the lower part 21*b*. The discharge pipe 21*c* has a discharge port 27 in the end. Such a housing 21 takes in air via the intake port 26 and sends out the air via the discharge port 27. The air is not restrictive, and other gases such as a drug-air mixture and oxygen may be used.

The rectifying member 22 is one shaped like a jet engine of gas turbine type, and is shaped to have a protruding end. This rectifying member 22 is arranged in the center of the intake port 26 so as to protrude from the intake port 26. The rectifying member 22 is connected and fixed to the rim of the intake port 26, for example, by three connection members 22*a*. A bearing 22*b* is embedded in the rectifying member 22, which also serves as a bearing for supporting the rotating shaft 28 of the impeller 23.

The impeller 23 shown in FIGS. 3 and 4 is arranged in the housing 21 so that its front side faces the intake port 26. More specifically, the impeller 23 is located closer to the intake port 26 in the direction of the rotating shaft 28 than a flow channel 32 to be described later is. This impeller 23 includes a plurality of blades 29 which are arranged around the rotating shaft 28, and a covering member 30 which covers the rear side (lower side in FIG. 3) of these plurality of blades 29. The impeller 23 is open on the intake port 26 side of the plurality of blades 29. In other words, no such member as the covering member 30 is arranged on the intake port 26 side of the plurality of blades 29. The plurality of blades 29 are integrally molded with the covering member 30.

These plurality of blades 29 face the inner periphery of the housing 21. The plurality of blades 29, if can be made as designed, preferably have a gap as close to 0 [mm] as possible with respect to the inner periphery of the housing 21.

Considering design errors, some gap (gap having the same size as the design errors: if the design errors are ±0.8 [mm], a gap of 0.8 [mm]) is preferably provided in view of avoiding collision between the blades 29 and the inner periphery of the housing 21. The covering member 30 has an umbrella-like shape protruding toward the intake port 26 side. In other words, the covering member 30 has a circular conical surface protruding toward the intake port 26 side. As a result, a space for arranging the motor 24 and the like is formed on the rear side (lower side in FIG. 3) of the covering member 30. The rotating shaft 28 of the impeller 23 is supported at both ends by the bearing 21*d* embedded in the housing 21 and the bearing 22*b* embedded in the rectifying member 22.

The motor 24 shown in FIG. 3 is arranged to be partly accommodated in the rear side (lower side in FIG. 3) of the impeller 23 (covering member 30). This motor 24 serves as a power source for rotating the impeller 23 about the rotating shaft 28. The number of rotations is preferably on the order of typical 10000 [rpm] to 20000 [rpm].

The partition member 25 is arranged on the rear side of the impeller 23 so that a slit d having a width w of 1.0 mm or less is formed to extend around along the inner periphery of the housing 21. The partition member 25 thereby partitions the rear side into a space 31 where the impeller 23 is arranged and the flow channel 32 which extends around along the slit d and leads to the discharge port 27. The slit d is preferably 0.6 mm or smaller in view of noise reduction.

The slit d is more preferably 0.6 mm, the largest, in view of a further reduction in energy loss. The reason is that as shown in FIG. 6, the noise cancelling level decreases gradually as the slit d becomes larger than 0.6 mm. Beyond 1.0 mm, the noise cancelling level drops sharply. The narrower the slit d becomes, the higher the energy loss is. Note that the slit d preferably has a width w smaller than or equal to 1.5% of the inner diameter D of the housing 21.

The flow channel 32 shown in FIGS. 3 and 5 is arranged in a concentric annular shape (annular shape having a constant cross-sectional area) so as to extend around the motor 24, and leads to the discharge pipe 21*c*. The flow channel 32 is arranged somewhat below (below in FIG. 3) the motor 24 so that the impeller 23, the motor 24, and the flow channel 32 are arranged in such order in the direction along the rotating shaft 28 of the impeller 23. This flow channel 32 most preferably has a perfect circular cross-sectional shape. A shape relatively long in the radial direction of the impeller 23 (horizontal direction in FIG. 3) is next preferred. In the present embodiment, the flow channel 32 employs a cross-sectional shape relatively long in the radial direction of the impeller 23 (in FIG. 3, $L_w > L_h$) for the purpose of miniaturization (thinning) in the height direction (vertical direction in FIG. 3). The cross-sectional area of the flow channel 32 is preferably set to be as large as possible.

Next, airflows in the blower 10 will be described with reference to FIGS. 3 and 5.

As shown in FIG. 3, the rotation of the impeller 23 moves the air in the space 31 where the impeller 23 is arranged in outward directions (right and left directions in FIG. 3). This reduces the air pressure on the inner periphery side (near the center in FIG. 3) of the space 31 where the impeller 23 is arranged. As a result, air is sucked into the space 31 in the housing 21 via the intake port 26. In other words, an airflow via the intake port 26 to the slit d in the housing 21 occurs.

As the air in the space 31 where the impeller 23 is arranged moves in the outward directions (right and left directions in FIG. 3), the air pressure on the outer periphery side (near the right and left sides in FIG. 3) of the space 31 increases. As a result, the air in the space 31 where the impeller 23 is arranged moves to the flow channel 32 via the slit d. In other words, an airflow from the space 31 where the impeller 23 is arranged to the flow channel 32 occurs.

The air moved to the flow channel 32 via the slit d moves along the wall surfaces, bottom surface, and ceiling surface of the flow channel 32. Due to the rotation of the impeller 23, the air moved to the flow channel 32 via the slit d is under a rotating force in the rotational direction of the impeller 23 (clockwise). As shown in FIG. 5, the air moved to the flow channel 32 via the slit d therefore rotates clockwise in the flow channel 32. The air rotated clockwise in the flow channel 32 is then passed through the discharge pipe 21*c* and sent into the chamber 11 via the discharge port 27 (see FIG. 1).

Return to FIG. 1. The chamber 11 serves as a path for the air sent out from the blower 10. This chamber 11 has a pair of air holes 11*a* to which the prongs 12 are attached, an air hole 11*b* which is opened and closed by the exhalation valve 15, and a connection port 11*c* to which the discharge port 27 of the blower 10 is connected. The pair of prongs 12 are nozzles to be inserted into the user's nose (see FIGS. 10 and 11(A)), and detachably attached to the air holes 11*a* of the chamber 11. As a result, the pair of prongs 12 guide the air sent from the blower 10 to the user's nasal cavity as intake air (see FIG. 9(B)). The pair of prongs 12 also guide the user's exhaled air to the chamber 11 (see FIG. 9(A)). The air pressure meter 13 is arranged in the chamber 11. This air pressure meter 13 measures the air pressure in the chamber 11, and outputs the measurement result as a signal to the control unit 16. The flowmeter 14 is arranged in the discharge pipe 21c of the blower 10. This flowmeter 14 measures the flow rate of the air sent out from the blower 10, and outputs the measurement result as a signal to the control unit 16.

The exhalation valve 15 is arranged in the chamber 11 so as to block the air hole 11b formed in the chamber 11. This exhalation valve 15 functions as a check valve for releasing the exhaled air guided into the chamber 11 and preventing its backflow. This exhalation valve 15 is a valve that has a monomorphic (unimorphic) structure formed by laminating a piezoelectric element 33, which makes a displacement according to the amount of voltage applied, with a metal plate 34, and has a cantilevered structure. The exhalation valve 15 therefore opens and closes as the piezoelectric element 33 makes a displacement to warp and straighten. More specifically, the piezoelectric element 33 of the exhalation valve 15 makes a displacement to draw apart from or approach to come into contact with the inner surface of the chamber 11, whereby the piezoelectric element 33 itself opens and closes the air hole 11b formed in the chamber 11.

Specifically, as shown in FIG. 9(A), in an initial state where no voltage is applied to the piezoelectric element 33, the exhalation valve 15 has a warped shape toward the inside of the exhalation path to open the air hole 11b formed in the chamber 11. As shown in FIG. 9(B), when a voltage is applied to the piezoelectric element 33, the exhalation valve 15 has a straightened shape to close the air hole 11b formed in the chamber 11. The exhalation valve 15 is fixed, for example, by a screw (not shown) or the like as appropriate.

It will be understood that while the exhalation valve 15 is described to have a monomorphic structure, a bimorphic structure formed by bonding two piezoelectric elements may be employed. The exhalation valve 15 preferably has a cantilever length of no less than 30 mm and no greater than 40 mm or so. The moving stroke of the exhalation valve 15 is preferably no less than 2 mm and no greater than 3 mm.

As shown in FIG. 7, the control unit 16 includes a CPU 36, a first storage medium 37, a second storage medium 38, a bus 39, and the like.

The CPU 36 is a so-called central processing unit, and executes various programs to implement various functions of the control unit 16. The first storage medium 37 is a so-called RAM (Random Access Memory), and is used as a work area of the CPU 36. The second storage medium 38 is a so-called ROM (Read Only Memory), and stores the programs to be executed by the CPU 36. The bus 39 serves as wiring that integrally connects the CPU 36, the first storage medium 37, the second storage medium 38, and the like and performs communication.

As shown in FIG. 8, the control unit 16 includes a sensing unit 41, an exhalation valve control unit 42, and a flow rate control unit 43 as functional components. The sensing unit 41 constantly obtains sensing data of the air pressure meter 13, and transmits the sensing data to the exhalation valve control unit 42. This sensing unit 41 further constantly obtains sensing data of the air pressure meter 13 and the flowmeter 14, and transmits the sensing data to the flow rate control unit 43. The exhalation valve control unit 42 refers to the sensing data of the sensing unit 41, and controls a control signal intended for the exhalation valve 15 so as to approach a target amount of opening. The flow rate control unit 43 refers to the sensing data of the sensing unit 41, and controls a control signal intended for the motor 24 of the blower 10 so as to approach a target flow rate value.

Note that in FIG. 1, the control unit 16 is shown outside the case 17 for ease of understanding. In fact, the control unit 16 is accommodated in the case 17.

Next, a control example of the exhalation valve 15 in the respiratory assistance device 1 will be described with reference FIGS. 1, 9(A), and 9(B).

When the user exhales, the pressure inside the chamber 11 increases. As the pressure inside the chamber 11 increases, the air pressure meter 13 senses the increased pressure value. The sensing data is output to the control unit 16. The control unit 16 controls the exhalation valve 15 on the basis of the sensing data. More specifically, the control unit 16 operates the exhalation valve 15 to open the air hole 11b of the chamber 11 (see FIG. 9(A)). The exhaled air is released via the air hole 11b.

The release of the exhaled air reduces the pressure inside the chamber 11. As the pressure inside the chamber 11 decreases, the air pressure meter 13 senses the decreased pressure value. The sensing data is output to the control unit 16. The control unit 16 controls the exhalation valve 15 on the basis of the sensing data. More specifically, the control unit 16 operates the exhalation valve 15 to close the air hole 11b (see FIG. 9(B)). This forms a closed space in the chamber 11 to enable an inhalation operation.

Next, when the user inhales, the pressure inside the chamber 11 decreases. As the pressure inside the chamber 11 decreases, the air pressure meter 13 senses the decreased pressure value. The sensing data is output to the control unit 16. The control unit 16 controls the motor 24 of the blower 10 on the basis of the sensing data. More specifically, the control unit 16 drives the motor 24 to send air from the blower 10 as inhaled air.

Since the air is sent from the blower 10 as inhaled air, the pressure inside the chamber 11 increases. As the pressure inside the chamber 11 increases, the air pressure meter 13 senses the increased pressure value. The sensing data is output to the control unit 16. The control unit 16 controls the motor 24 of the blower 10 on the basis of the sensing data. More specifically, the control unit 16 stops the motor 24 to stop sending air from the blower 10 as inhaled air. Subsequently, the exhalation operation and the inhalation operation are repeated in the same manner.

Return to FIG. 1. The case 17 accommodates the blower 10, the chamber 11, the control unit 16, etc. Air holes 17a and 17b are formed in the case 17 so as to correspond to the air holes 11a and 11b of the chamber 11. The prongs 12 are detachably attached to the pair of air holes 17a. The air hole 17b functions as an exhalation path. The case 17 also has an inlet port (not shown) for letting air into the intake port 26 of the blower 10. The inlet port is preferably filled with a porous member (such as open cell sponge) for preventing dust intrusion. This porous member also has a sound absorption effect.

Next, a use state of the respiratory assistance device 1 will be described with reference to FIGS. 10, 11(A), and 11(B).

As shown in FIGS. 10 and 11(A), the respiratory assistance device 1 is used with the pair of prongs 12 inserted into the nasal cavity. A portion of the case 17 where the blower 10 is accommodated is placed on the user's mouth so as to be in contact with the user's mouth. In other words, the blower 10 is indirectly in contact with the user's mouth. As shown in FIG. 11(A), the center of gravity of the blower 10 is located $R_1$ [mm] from the center axis C of the user's body. On the other hand, as shown in FIG. 11(B), the center of gravity of a conventional respiratory assistance device 100 is located $R_2$ [mm]($>R_1$) from the center axis C of the user's body. This respiratory assistance device 100 has a blower integrally formed outside the mask.

As described above, according to the respiratory assistance device 1, the distance from the center axis of the user's body to the center of gravity of the blower 10 can be reduced as compared to heretofore. This can reduce the moment of the blower 10 when the user in bed turns over or turns his/her face. Since the blower 10 is placed on the mouth, the user can turn over or turn his/her face without pressing the blower 10 against the pillow with his/her face. As a result, the burden on the user can be reduced.

Suppose that the blower is placed on cheeks. In such a case, the blower can be pressed against the pillow and the like by the cheeks (face) when the user turns over or turns his/her face. This is burdensome to the user. In other words, the blower 10 essentially needs to be placed on the centerline of the body. Among positions on the centerline, the blower 10 is placed on the mouth which is less disturbing to the user.

The blower 10 (the portion of the case 17 where the blower 10 is accommodated) can hold the user's mouth to help to keep the mouth closed. This produces a mouth-closed state which is desirable during nasal breathing, whereby the burden on the user is reduced. Note that the contact with the mouth may be either direct or indirect.

The blower 10 employs the two-stage structure including the space 31 where the impeller 23 is arranged and the flow channel 32 which leads to the discharge port 27. The airflow taken in via the intake port 26 can thus be separated from the airflow to be sent out via the discharge port 27. This can avoid collision between the air taken in via the intake port 26 and the airflow to be sent out via the discharge port 27. In other words, the occurrence of noise due to the collision of the airflows can be prevented.

The flow of the air through the slit d connecting the space 31 where the impeller 23 is arranged and the flow channel 32 produces noise. Such noise can cancel other noises occurring from the rotation of the impeller 23. As a result, a burden on the user due to noise can be reduced.

The air flowing from the space 31 where the impeller 23 is arranged into the flow channel 32 moves smoothly along the side surfaces, bottom surface, and ceiling surface of the flow channel 32. As a result, the occurrence of a turbulent flow can be prevented. This can consequently prevent the occurrence of noise.

The flow channel 32 is arranged to extend around the motor 24. This allows miniaturization in the direction of the rotating shaft 28 of the impeller 23.

Moreover, the rectifying member 22 is arranged to protrude from the intake port 26. This can prevent the collision of air near the intake port 26 as compared to the case when there is no rectifying member or the case when the rectifying member is contained inside without protruding from the intake port 26. For example, if there is no rectifying member, the air taken in via the intake port 26 collides with the impeller 23 and the rotating shaft 28. The foregoing blower 10 causes no such collision. If the rectifying member is contained inside without protruding from the intake port 26, the rectifying member narrows the interior of the housing 21 so sharply that the air taken into the housing 21 collides. The foregoing blower 10 causes no such collision. As a result, the occurrence of noise can be prevented.

The rectifying member 22 supports one end of the rotating shaft 28 of the impeller 23, whereby vibrations of the impeller 23 can be prevented. This can consequently prevent the occurrence of noise. Since the rectifying member 22 also functions to support one end of the rotating shaft 28 of the impeller 23, the parts count can be reduced for weight saving and miniaturization. The respiratory assistance device 1 can thus be easily carried about on overnight trips, business trips, and the like.

The impeller 23 is open on the intake port 26 side of the plurality of blades 29. This allows weight saving and miniaturization as compared to the case when a covering member that covers the intake port 26 side of the plurality of blades 29 is provided. The respiratory assistance device 1 can thus be easily carried about on overnight trips, business trips, and the like.

Moreover, the covering member 30 has a circular conical surface protruding toward the intake port 26 side, so that the air taken into the housing 21 via the intake port 26 can flow smoothly along the covering member 30. The air taken into the housing 21 via the intake port 26 can thus be prevented from colliding with the covering member 30. This can consequently prevent the occurrence of noise.

The exhalation valve 15 includes the piezoelectric element 33, and the amount of opening thereof can be finely adjusted. This can avoid a sharp change in the flow rate of the exhaled air released via the exhalation valve 15. In other words, a sharp change in the air pressure in the path from the blower 10 to the user's nose can be prevented. This can prevent an increase in the burden on the user.

The exhalation valve 15 can be closed so that the interior of the path becomes air tight during breathing in. The amount of gas leaking via the exhalation valve 15 can thus be reduced. Beside, since the exhalation valve 15 includes the piezoelectric element 33, responsiveness is high and the burden on the user is small. Specifically, if a solenoid valve is used as the exhalation valve 15, the exhalation valve opens and closes in about 8 msec to 10 msec of time. If the exhalation valve 15 includes the piezoelectric element 33 like the foregoing embodiment, the exhalation valve 15 can open and close in a time as short as about 100 μsec.

Since the exhalation valve 15 includes the piezoelectric element 33, the exhalation valve 15 has a longer endurance time and is more difficult to break than when a solenoid valve is used as the exhalation valve 15. Moreover, since the exhalation valve 15 includes the piezoelectric element 33, the respiratory assistance device 1 can be miniaturized and reduced in weight as compared to cases such as when a solenoid valve is used as the exhalation valve 15. The gravitational force of the respiratory assistance device 1 acting on the face of the user can thus be reduced to reduce the burden on the user.

Patients with sleep apnea syndrome and the like can use the respiratory assistance device 1 as a home care ventilator.

Second Embodiment

Figure 12:
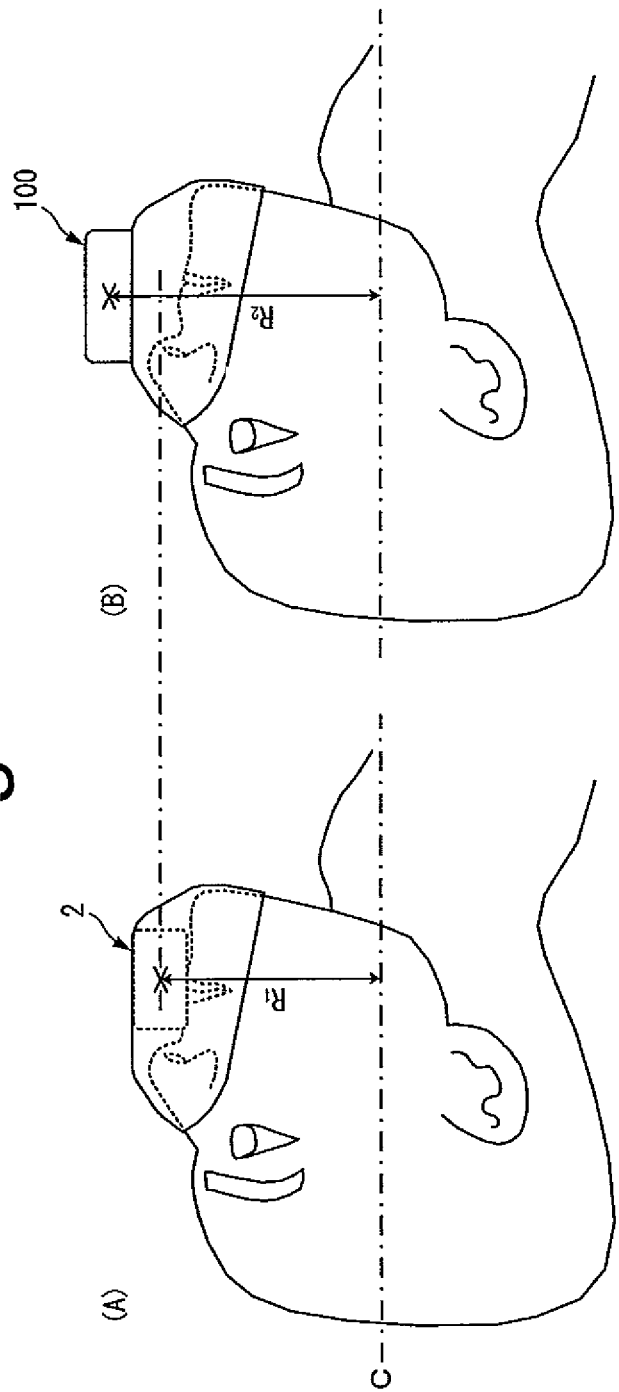
FIGS. 12(A) and 12(B) are diagrams showing use states of respiratory assistance devices for explaining moment.

Next, a configuration of a respiratory assistance device 2 according to a second embodiment of the present invention will be described with reference to FIGS. 12(A) and 12(B). FIGS. 12(A) and 12(B) are diagrams showing use states of respiratory assistance devices for explaining moment. FIG. 12(A) shows a case with the respiratory assistance device 2. FIG. 12(B) shows a case with the conventional respiratory assistance device 100.

The following description deals only with characteristic parts of the respiratory assistance device 2. A description of the same configuration, operation, and effects as those of the respiratory assistance device 1 will be omitted.

As shown in FIG. 12(A), the respiratory assistance device 2 includes a blower that is integrally arranged inside a mask. The user wears the mask to use this respiratory assistance device 2. The blower is placed on the user's mouth so as to be in contact with the user's mouth. As shown in FIG. 12(A), the center of gravity of the blower is located $R_1$ [mm] from the center axis C of the user's body. On the other hand, as shown in FIG. 12(B), the center of gravity of the conventional respiratory assistance device 100 is located $R_2$ [mm]($>R_1$) from the center axis C of the user's body. This respiratory assistance device 100 includes a blower integrally arranged outside the mask.

Next, experiments 1 to 4 will be described in order.

Figure 13:
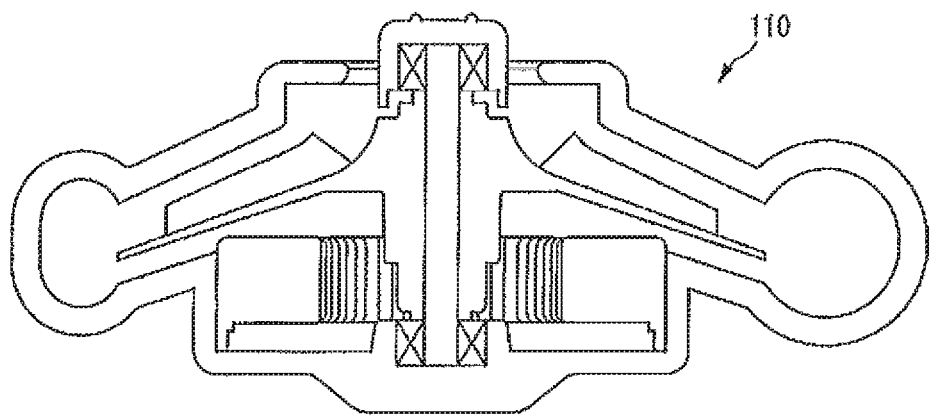
FIG. 13 is a sectional view of a blower according to a comparative example.

Experiments 1 and 2 were comparative experiments using a blower 110 serving as a master shown in FIG. 13. Like the blower 10 according to the foregoing respective embodiments, the blower 110 is a power source needed for a respiratory assistance device which a patient with respiration disorder uses. The blower 110 sends air to produce a positive pressure in the airway.

Unlike the blower 10 according to the foregoing respective embodiments, this blower 110 does not include a rectifying member. In the blower 110, the gap between the blades and the inner periphery of the housing is set to 1.9 [mm]. The blower 110 has a single-stage structure in which the space where the impeller is arranged and the flow channel leading to the discharge port are continuous. In other words, the blower 110 includes no configuration corresponding to the slit d of the blower 10 according to the foregoing respective embodiments. The blower 110 further has a scroll shape (spiral shape) such that the cross-sectional area of the flow channel increases gradually toward the discharge port. In the blower 110, the impeller, the flow channel, and the motor are arranged in such order in a direction along the rotating shaft of the impeller. The blower 110 is one used in a continuous positive airway pressure unit (trade name: Jusmine) sold by Metran Co., Ltd. (Kawaguchi-shi, Saitama).

Experiment 3 compared the blower 10 according to the foregoing respective embodiments with blowers according to modifications thereof. Experiment 4 was a comparative experiment of the blower 10 according to the foregoing respective embodiments with a competitor's product.

Experiment 1

Initially, experiment 1 which examined noise reduction by the rectifying member will be described. This experiment 1 compared the noise level [dB] of the blower 110 serving as a master with that of the blower 110 to which the rectifying member was attached. As a result, the attachment of the rectifying member reduced the noise level by approximately 1.7 [dB] to 2.5 [dB]. The acoustic power [dB] in middle and high ranges of approximately 750 [Hz] and above decreased.

Experiment 2

Experiment 2 which examined the effect of the gap between the blades and the inner periphery of the housing on noise will be described. This experiment 2 compared the noise level [dB] of the blower 110 serving as a master with that of the blower 110 to which the rectifying member was attached and in which the gap between the blades and the inner periphery of the housing was reduced to 0.8 [mm]. As a result, the attachment of the rectifying member and the reduction of the gap between the blades and the inner periphery of the housing to 0.8 [mm] reduced the noise level by approximately 3.8 [dB] to 4.2 [dB]. The attachment of the rectifying member and the reduction of the gap between the blades and the inner periphery of the housing to 0.8 [mm] reduced the acoustic power [dB] in middle and low ranges of approximately 3200 [Hz] and below in particular. In consideration of experiment 1, it is shown that the reduction of the gap between the blades and the inner periphery of the housing to 0.8 [mm] reduced the acoustic power [dB] in the middle and low ranges.

Experiment 3

Experiment 3 which examined the effect of the slit extending around along the inner periphery of the housing on noise will be described. This experiment 3 compared the noise level [dB] of the blower 10 according to the foregoing embodiments with that of the blower 10 in which the width w of the slit d between the partition member 25 and the inner periphery of the housing 21 was changed to 1.5 [mm] or 2.0 [mm]. In other words, the noise levels [dB] with a slit d of 1.0 [mm], 1.5 [mm], and 2.0 [mm], respectively, were compared. As a result, if the width w of the slit d between the partition member 25 and the inner periphery of the housing 21 was reduced to 1.0 [mm], the sound level decreased by approximately 0.9 [dB] to 3.2 [dB] as compared to the cases with 1.5 [mm] and 2.0 [mm], respectively. Meanwhile, the noise level did not vary much between when the width w of the slit d was set to 1.5 [mm] and 2.0 [mm]. The reduction of the width w of the slit d between the partition member 25 and the inner periphery of the housing 21 to 1.0 [mm] reduced the acoustic power [dB] generally across the entire range.

Experiment 4

Experiment 4 which made a comparison with the noise level of a competitor's product will be described. This experiment 4 compared the noise level [dB] of the blower 10 according to the foregoing respective embodiments with that of a blower (see Japanese Patent No. 4497809) that is used for an automatic continuous positive airway pressure unit (trade name: S9Elite) sold by ResMed Limited (Australia) and ResMed Inc. (Bunkyo-ku, Tokyo), which achieves the world's lowest level of noise at the time of filing of the present application. As compared to the foregoing competitor's product achieving the world's lowest level of noise, the blower 10 according to the foregoing respective embodiments provided a noise level approximately 1.4 [dB] to 3.0 [dB] lower. As compared to the foregoing competitor's product achieving the world's lowest level of noise, the blower 10 according to the foregoing respective embodiments reduced the acoustic power [dB] in a middle range of not lower than approximately 750 [Hz] and not higher than approximately 6400 [Hz].

The present invention is not limited to the foregoing respective embodiments, and various modifications may be made without departing from the gist and technical concept thereof.

More specifically, in the foregoing respective embodiments, the positions, sizes (dimensions), shapes, materials, directions, and numbers of the respective components may be changed as appropriate.

In the foregoing respective embodiments, the blower for sending air has been described by using the blower 10 including the impeller 23 as an example. However, the present invention is not limited thereto, and a micro pump or the like may be included. A micro pump is a pump using a diaphragm to which a piezoelectric element is fixed. A micro pump has the following structure.

Next, a configuration of a micro pump 200 will be described with reference to FIGS. 14(A) and 14(B).

The micro pump 200 shown in FIG. 14(A) is one proposed by Patent Document WO 2008/069266. The micro pump 200 includes a primary blower chamber 201 and a secondary blower chamber 202 formed outside the primary blower chamber 201.

The primary blower chamber 201 includes a piezoelectric element 203 which serves as a vibration source, a diaphragm 204 to which the piezoelectric element 203 is fixed, and a vibrating frame 205 which forms a space with this diaphragm 204. The vibrating frame 205 has an opening 206 for moving fluid inside and outside of the primary blower chamber 201. The secondary blower chamber 202 has a suction port 207 on the diaphragm 204 side and a discharge port 208 opposite to the opening 206.

In the foregoing micro pump 200, when the piezoelectric element 203 makes the diaphragm 204 resonate, the fluid moves between the primary blower chamber 201 and the secondary blower chamber 202. The resulting fluid resistance makes the vibrating frame 205 resonate. The resonance of the diaphragm 204 and the vibrating frame 205 sucks in the fluid via the suction port 207 and releases the fluid via the discharge port 208.

Such a micro pump 200 is suitable for use as a blower for conveying gas, and can perform conveyance without using a check valve. The micro pump 200 has a box-like shape with outer dimensions of about 20 mm×20 mm×2 mm and is extremely small. With a 26-kHz input sine wave of 15 Vpp (Volt peak to peak), the micro pump 200 can convey air up to approximately 1 L/min (at a static pressure of 0 Pa) and can provide a static pressure of up to approximately 2 kPa (at a flow rate of 0 L/min).

Since the micro pump 200 conveys fluid by the vibrations of the diaphragm 204 caused by the piezoelectric element 203, the conveyable volume of the fluid is naturally limited. Such a static pressure/flow rate characteristic also traces a straight line as shown in FIG. 14(B). For example, to obtain a static pressure of approximately 1 kPa, the flow rate is 0.5 L/min.

If the Vpp of the input sine wave is changed to 10 or 20, the amplitude of the piezoelectric element 203 changes. This can change the flow rate and the pressure. That is, the Vpp of the input sine wave can be smoothly changed to change the flow rate and the pressure smoothly. Alternatively, the frequency of the input sine wave can be changed to change the flow rate and the pressure. That is, the frequency of the input sine wave can be smoothly changed to change the flow rate and the pressure smoothly. Note that the flow rate and the pressure have their limits depending on the capability of the piezoelectric element 203 and the strength and durability of the members. The micro pump 200 is usually used with the rated Vpp and frequency.

The foregoing description has dealt with a monomorphic (unimorphic) structure in which one piezoelectric element 203 is bonded to the diaphragm 204. It will be understood that a bimorphic structure using two piezoelectric elements bonded to increase the amount of vibrations may be employed.

REFERENCE SIGNS LIST 1, 2 Respiratory assistance device
10 Blower
11 Chamber (path)
12 Prong
15 Exhalation valve
23 Impeller
25 Partition member
26 Intake port
27 Discharge port
31 Space
32 Flow channel
33 Piezoelectric element
200 Micro pump (blower)
d Slit

The invention claimed is:

1. A respiratory assistance device comprising:
a prong that is an airway to be attached to a nose of a user; and
a blower that is connected to the prong and is adapted to send gas to a nasal cavity of the user via the prong, wherein
the blower is adapted to be placed directly on a mouth of the user;
wherein the blower is adapted to be in contact with the mouth of the user; and
wherein the blower is adapted to keep the mouth of the user closed.

2. The respiratory assistance device according to claim 1, wherein
the blower includes:
a housing including an intake port from which the gas is taken in, a flow channel that is arranged to extend within the housing and through which the gas taken in via the intake port flows, and a discharge port that sends the gas flowing through the flow channel toward the prong;
an impeller that is arranged in the housing so that a front side thereof faces the intake port; and
a partition member that is arranged on a rear side of the impeller so that a slit is formed along an inner periphery of the housing, thereby partitioning the housing into a front space where the impeller is arranged and a rear space wherein the flow channel extends along the slit.

3. A method of using the respiratory assistance device of claim 1, comprising:
attaching the prong to the nose of the user;
using the blower to send gas to the nasal cavity of the user via the prong; and
placing the blower directly on the mouth of the user.

4. A respiratory assistance device comprising:
a prong that is an airway to be attached to a nose of a user;
a blower that is connected to the prong and is adapted to send gas to a nasal cavity of the user via the prong, wherein
the blower is adapted to be placed directly on a mouth of the user; and
an exhalation valve that is arranged to cover an air hole formed in a path from the blower to the nose of the user, and wherein:
the exhalation valve releases exhaled air through the air hole into the atmosphere directly and prevents backflow of the exhaled air to the blower;
the exhalation valve includes a piezoelectric element that makes a displacement according to an amount of voltage applied; and the piezoelectric element makes the displacement to draw apart from or approach to make contact with a surface constituting the path, whereby the piezoelectric element itself opens and closes the air hole.

5. The respiratory assistance device according to claim 4, wherein the exhalation valve makes the displacement within the path.

6. A method of using a respiratory assistance device comprising:
　　attaching a prong that is an airway to a nose of a user;
　　connecting a blower to the prong;
　　using the blower to send gas to a nasal cavity of the user via the prong;
　　placing the blower directly on a mouth of the user; and
　　keeping the mouth of the user closed with the blower.

* * * * *